United States Patent
Okubo et al.

(10) Patent No.: US 8,440,555 B2
(45) Date of Patent: May 14, 2013

(54) METHOD FOR ANALYZING ELECTROLYTIC COPPER PLATING SOLUTION

(75) Inventors: Toshikazu Okubo, Tokyo (JP); Katsuyoshi Naoi, Tokyo (JP); Yuka Yamada, Tokyo (JP)

(73) Assignee: Toppan Printing Co., Ltd. (JP)

( * ) Notice: Subject to any disclaimer, the term of this patent is extended or adjusted under 35 U.S.C. 154(b) by 217 days.

(21) Appl. No.: 12/903,090

(22) Filed: Oct. 12, 2010

(65) Prior Publication Data

US 2011/0025294 A1 Feb. 3, 2011

Related U.S. Application Data

(63) Continuation of application No. 10/550,153, filed as application No. PCT/JP2004/003934 on Mar. 23, 2004, now Pat. No. 7,820,535.

(30) Foreign Application Priority Data

Mar. 25, 2003 (JP) ................................ 2003-082037
Oct. 9, 2003 (JP) ................................ 2003-350544

(51) Int. Cl.
*H01L 21/20* (2006.01)
(52) U.S. Cl.
USPC ............. 438/584; 438/637; 205/81; 205/123
(58) Field of Classification Search .................... 438/17, 438/687, 584, 637; 205/81, 123, 182; 257/E21.577, 257/E21.585
See application file for complete search history.

(56) References Cited

U.S. PATENT DOCUMENTS

| | | | |
|---|---|---|---|
| 5,223,118 A | 6/1993 | Sonnenberg et al. | |
| 6,511,588 B1 | 1/2003 | Kobayashi et al. | |
| 6,709,568 B2 | 3/2004 | Han et al. | |
| 6,846,227 B2 | 1/2005 | Sato et al. | |
| 6,921,551 B2 | 7/2005 | Basol | |
| 7,192,335 B2 | 3/2007 | Lee et al. | |
| 7,820,535 B2 * | 10/2010 | Okubo et al. | 438/584 |
| 2003/0058629 A1 | 3/2003 | Hirai et al. | |

FOREIGN PATENT DOCUMENTS

| | | |
|---|---|---|
| JP | 05080028 | 3/1993 |
| JP | 2001152398 | 6/2001 |
| WO | WO 01/29548 | 4/2001 |

OTHER PUBLICATIONS

Notice of Office Action issued by Taiwanese Intellectual Property Office on Oct. 30, 2009 (4 pgs), including English translation (7 pgs).
Second Notice of Office Action issued by Taiwanese Intellectual Property Office on Jun. 10, 2010, (2 pgs), including English translation (4 pgs).
Notice of First Office Action issued by State Intellectual Property Office of the People's Republic of China on Sep. 19, 2008 (8 pgs), including English translation (23 pgs).

(Continued)

*Primary Examiner* — J. Christopher Ball
(74) *Attorney, Agent, or Firm* — Squire Sanders (US) LLP (57) ABSTRACT

Effective fillability and the uniformity electrodeposition of a copper electroplating solution is judged by determining the time-dependent potential change thereof at a cathode current density of 0.1-20 A/dm$^2$. The potential change is determined at a working electrode rotation of 100-7500 rpm, and the fillability with the solution is judged from the curve profile. In an embodiment of the present invention, the fillability is judged by obtaining the potential change speed in the initial stage of electrolysis and the potential convergent point from the time-dependent potential change curve for a predetermined period of time after the start of the electrolysis.

1 Claim, 9 Drawing Sheets

OTHER PUBLICATIONS

Notice of Second Office Action issued by State Intellectual Property Office of the People's Republic of China on Mar. 13, 2009 (6 pgs), including English translation (17 pgs).

Notice of Third Office Action issued by State Intellectual Property Office of the People's Republic of China on Jun. 19, 2009 (3 pgs), including English translation (9 pgs).

Notice of Reasons for Rejection Issued by JPO on Nov. 10, 2009 (2 pgs) including English translation (4 pgs).

Notification of Reasons for Refusal Issued by Korean Intellectual Property Office on Jan. 12, 2011 (8 pgs), including English translation (26 pgs).

* cited by examiner

METHOD FOR ANALYZING ELECTROLYTIC COPPER PLATING SOLUTION

CROSS REFERENCE TO RELATED APPLICATION

This application is a divisional of application Ser. No. 10/550,153, filed on Sep. 20, 2005, which is now U.S. Pat. No. 7,820,535, which claims priority to Japanese application Nos. 2003-082037 filed Mar. 25, 2003 and 2003-350544 filed Oct. 9, 2003, and for which claimed domestic priority under 371 to PCT/JP04/003934 dated Mar. 23, 2004.

BACKGROUND OF THE INVENTION

1. Field of the Invention
2. Technical Field

The present invention relates to a method for analyzing a copper electroplating solution used in copper electroplating for filling a copper metal in a via-hole or a trench installed in printed circuit boards, semiconductor package substrates or semiconductor products such as semiconductor substrates, and to an apparatus for the analysis and to a method for producing a semiconductor product. The present application is based on Japanese Patent Application No. 2003-082037 and Japanese Patent Application No. 2003-350544, of which the disclosures are hereby incorporated.

3. Background Art

In general, additives are used in a copper electroplating solution. Additives include a promoter and a retardant, and when added to a plating solution, then the plating on the bottom of a via-hole is promoted while that outside the via-hole is retarded whereby the via-hole is filled with a plating metal. To attain the phenomenon, the promoter and the retardant used must be well balanced in point of their effects, and the concentration control of the additive components is important.

One method proposed for the concentration control of additives is CV (cyclicvoltammetry) (e.g., see R. Haak, C. Ogdan, D. Trench: Plating 64 (4), April 1981). The basis of CV analysis is that, when a voltage is imparted to the inactive electrode in a plating solution and the potential is linearly scanned, then the additive in the solution changes the polarization for copper deposition reaction thereby having an influence on the amount of the deposited copper. The amount of the deposited copper plating thus measured is in proportion to the quantity of electricity having passed through the inactive electrode, and therefore, when the quantity of electricity is measured, then the effect of the additive to change the polarization may be evaluated.

A method that employs this conception is CVS (cyclic voltammetry stripping). Periodically changing the potential applied to an electrode, copper plating on the surface of the electrode and stripping from it is repeated, and the quantity of electricity for stripping is measured as a criterion for the amount of the plating copper. From the ratio of the plating amount with a solution having a known concentration and that with the in-field solution to be analyzed, the additive concentration in the in-field solution is computed.

In spite of the assertion, that CV is usable as an additive control apparatus and of the effectiveness of commercially-available CVS apparatus, there are posed many technical problems. For example, in copper electroplating for filling vias, there is a problem in that the fillability with the plating solution is worsen with the lapse of time after the preparation of the plating bath, even though the additive concentration in the solution is controlled through CVS analysis. This will be because, though the additive component decomposes during plating and therefore its effect reduces, even the component having such a reduced effect may be detected as the additive concentration in CVS analysis.

DISCLOSURE OF THE INVENTION

The first aspect of the invention is a method for analyzing a copper electroplating solution containing an additive, which comprises determining the time-dependent potential change at a cathode current density of 0.1-20 A/dm$^2$ to thereby judge the fillability with the copper electroplating solution.

The second aspect of the invention is the method for analyzing a copper electroplating solution of claim 1, wherein the time-dependent potential change determination is effected while the rotation of the working electrode is controlled in the range of 100-7500 rpm.

The third aspect of the invention is the method for analyzing a copper electroplating solution of claim 1, wherein the fillability is judged by obtaining the potential change speed in the initial stage of electrolysis and the potential convergent point from the time-dependent potential change curve for a predetermined period of time after the start of the electrolysis.

The 4$^{th}$ aspect of the invention is the method for analyzing a copper electroplating solution of the first to the third aspects of the invention, wherein the fillability is judged by approximating the time-dependent potential change curve for a predetermined period of time after the start of the electrolysis, according to the Boltzmann's function represented by the following numerical formula (1), to thereby obtain the potential change speed dx:

$$y = \frac{A_1 - A_2}{1 + e^{\frac{x-x_0}{dx}}} + A_2. \tag{1}$$

The 5$^{th}$ aspect of the invention is an apparatus for analyzing a copper electroplating solution, which comprises using the method for analyzing a copper electroplating solution of any one of the 1$^{st}$ to 4$^{th}$ aspects of the invention.

The 6$^{th}$ aspect of the invention is a method for fabricating a semiconductor product, which comprises using the method for analyzing a copper electroplating solution of any one of 1$^{st}$ to 4$^{th}$ aspects of the invention and controlling the condition of the solution so as to make the time-dependent change curve profile of the solution near to that of the original solution when it is judged that the condition of the solution is not good and satisfactory fillability could not be obtained.

The 7$^{th}$ aspect of the invention is a method for analyzing a copper electroplating solution used in copper electroplating for filling a copper metal in a via-hole or a trench installed in a semiconductor product, which comprises using an electrochemical cell composed of a working electrode (rotary electrode), a reference electrode and a copper electrode (counter electrode) for a copper electroplating solution, electrolyzing the solution with the working electrode (rotary electrode) as a cathode so as to make the cathode current density controlled in the range of 0.1-20 A/dm$^2$, determining the time-dependent potential change between the cathode and the reference electrode for a predetermined period of time after the start of the electrolysis, and judging the fillability with the copper electroplating solution from the time-dependent change curve profile.

The 8$^{th}$ aspect of the invention is the method for analyzing a copper electroplating solution of the 7$^{th}$ aspect of the invention, wherein the time-dependent potential change determination is effected while the rotation of the working electrode is controlled in the range of 100-7500 rpm.

The 9th aspect of the invention is the method for analyzing a copper electroplating solution of the 7th or the 8th aspect of the invention, wherein the fillability is judged by obtaining the potential change speed in the initial stage of electrolysis and the potential convergent point from the time-dependent potential change curve for a predetermined period of time after the start of the electrolysis.

The 10th aspect of the invention is the method for analyzing a copper electroplating solution of the 7th to the 9th aspects of the invention, wherein the fillability is judged by approximating the time-dependent potential change curve for a predetermined period of time after the start of the electrolysis, according to the Boltzmann's function represented by the following numerical formula (1), to thereby obtain the potential change speed dx in the initial stage and the potential convergent point $A_2$:

$$y = \frac{A_1 - A_2}{1 + e^{\frac{x - x_0}{dx}}} + A_2. \tag{1}$$

The 11th aspect of the invention of claim 11 is an apparatus for analyzing a copper electroplating solution, which comprises using the method for analyzing a copper electroplating solution of any one of the 7th to 10th aspects of the invention.

The 12th aspect of the invention is a method for fabricating a semiconductor product, which comprises using the method for analyzing a copper electroplating solution of any one of the 7th to the 10th aspects of the invention and controlling the condition of the solution so as to make the time-dependent change curve profile of the solution near to that of the original solution when it is judged that the condition of the solution is not good and satisfactory fillability could not be obtained.

The 13th aspect of the invention is a method for analyzing a copper electroplating solution containing an additive, which comprises using an electrochemical cell composed of a working electrode (rotary electrode), a reference electrode and a copper electrode (counter electrode) for a copper electroplating solution, electrolyzing the solution with the working electrode (rotary electrode) as a cathode so as to make the cathode current density controlled in the range of 0.1-20 A/dm², and determining the time-dependent potential change for a predetermined period of time after the start of the electrolysis to thereby judge the uniformity of electrodeposition (film properties and film thickness uniformity) with the solution.

The 14th aspect of the invention is the method for analyzing a copper electroplating solution of the 13th aspect of the invention, wherein the time-dependent potential change determination is effected while the rotation of the working electrode (rotary electrode) is controlled in the range of 100-7500 rpm.

The 15th aspect of the invention is the method for analyzing a copper electroplating solution of the 13th or the 14th aspect of the invention, wherein the fillability is judged by obtaining the potential change speed in the initial stage of electrolysis and the potential convergent point from the time-dependent potential change curve for a predetermined period of time after the start of the electrolysis.

The 16th aspect of the invention is the method for analyzing a copper electroplating solution of the 13th to the 15th aspects of the invention, wherein the uniformity of electrodeposition (film properties and film thickness uniformity) is quantitatively judged by approximating the time-dependent potential change curve according to the Boltzmann's function represented by the following numerical formula (1), to thereby obtain the potential change speed dx:

$$y = \frac{A_1 - A_2}{1 + e^{\frac{x - x_0}{dx}}} + A_2. \tag{1}$$

The 17th aspect of the invention is an apparatus for analyzing a copper electroplating solution, which comprises using the method for analyzing a copper electroplating solution of any one of the 13th to the 16th aspects of the invention.

The 18th aspect of the invention is a method for fabricating a semiconductor product, which comprises using the method for analyzing a copper electroplating solution of any one of the 13th to the 16th aspects of the invention and controlling the condition of the solution so as to make the time-dependent change curve profile of the solution near to that of the original solution when it is judged that the condition of the solution is not good and satisfactory fillability could not be obtained.

The 19th aspect of the invention is a method for analyzing a copper electroplating solution used in copper electroplating for filling a copper metal in a via-hole or a trench installed in a semiconductor product, which comprises using an electrochemical cell composed of a working electrode (rotary electrode), a reference electrode and a copper electrode (counter electrode) for a copper electroplating solution, electrolyzing the solution with the working electrode (rotary electrode) as a cathode so as to make the cathode current density controlled in the range of 0.1-20 A/dm², controlling the rotation of the working electrode (rotaryelectrode) in two stages falling within a range of 0-7500 rpm, determining the time-dependent potential change between the cathode and the reference electrode at different rotations, and comparing the time-dependent change curves with each other to thereby judge the fillability with the copper electroplating solution.

The 20th aspect of the invention is an apparatus for analyzing a copper electroplating solution, which comprises using the method for analyzing a copper electroplating solution of the 19th aspect of the invention.

The 21st aspect of the invention is a method for fabricating a semiconductor product, which comprises using the method for analyzing a copper electroplating solution of the 19th aspect of the invention and controlling the condition of the solution so as to make the time-dependent change curve profile of the solution near to that of the original solution when it is judged that the condition of the solution is not good and satisfactory fillability could not be obtained.

BEST MODE FOR CARRYING OUT THE INVENTION

The method for analyzing a copper electroplating solution of the $1^{st}$ to the $6^{th}$ aspects of the invention and the $7^{th}$ to $12^{th}$ aspects of the invention is described with reference to one embodiment thereof. Herein investigated is a method capable of differentiating additive-containing copper electroplating solutions from each other as to whether they are good or not good in point of the fillability thereof. The composition of the plating solution comprises 200 g/liter of copper sulfate, 100 g/liter of sulfuric acid, and 50 mg/liter of chloride ion. As the additives to it, used are a promoter containing SPS (bis(3-sulfopropyl)disulfide disodium) and a retardant containing PEG (polyethylene glycol). A suitable amount of a quaternary ammonium salt is added to it as a leveler.

When a phosphorus-containing copper anode is dipped in the copper electroplating solution for a long period of time with no current applied thereto, then the fillability with the solution for plating lowers. This is similar to the phenomenon that may occur in a case where an excess promoter is added to the plating solution. It is believed that a substance having a significant promoting effect may be formed in the solution through the reaction between the metal copper in the surface of the phosphorus-containing copper anode and the additive component. However, when the concentration of the additive component of the plating solution is measured through CVS, then both the promoter and the retardant may have nearly the same concentration before and after dipping a phosphorus-containing copper anode in the solution.

As the solution having good fillability, used is a fresh solution containing a standard amount of an additive and having been just prepared (hereinafter this is referred to as "fresh solution"). As the solution having bad fillability, used is a solution containing a standard amount of an additive in which a phosphorus-containing copper anode was dipped (hereinafter this is referred to as "phosphorus-containing copper-dipped solution"). This is because, when a phosphorus-containing copper is dipped therein, the fillability with the plating solution worsens. The phosphorus-containing copper-dipped solution is prepared by setting a controlled area of 100 $cm^2$/liter of a phosphorus-containing copper plate in one liter of the fresh solution, and then statically keeping it as such for 2, 4, 6, 8 and 24 hours.

In the $1^{st}$ to the $6^{th}$ aspects and the $7^{th}$ to the $12^{th}$ aspects of the invention, used is an electrochemical cell composed of a working electrode (rotary electrode), a reference electrode and a copper electrode (counter electrode). In this, the working electrode (rotary electrode) serves as a cathode and the rotation of the working electrode (rotary electrode) is controlled in the range of 100-7500 rpm; and an electroplating solution is electrolyzed at a constant current so as to make the cathode current density controlled in the range of 0.1-20 $A/dm^2$, and the time-dependent potential change between the cathode and the reference electrode is determined. As the reference electrode, used is Ag/AgCl or $Hg/Hg_2SO_4$, and as the working electrode (rotary electrode), used is a platinum disc electrode, to which, however, the invention should not be limited.

The optimum cathode current density at which the difference between a fresh solution and a phosphorus-containing copper-dipped solution could be known varies depending on the balance of the additive components in the solutions, and therefore it is desirable that the optimum cathode current density is defined individually for each plating solution. In general, the cathode current density may controlled in the range of 0.1-20 $A/dm^2$, preferably between 0.1-5 $A/dm^2$. If it is lower than 0.1 $A/dm^2$, then a difference will hardly appear in the measurement results between the solution having good fillability and the solution having poor fillability; but if higher than 5 $A/dm^2$, then the potential could hardly become stable.

The rotation of the working electrode during measurement is preferably at least 100 rpm at which the effect of rotation may appear. However, if the rotation is more than 7500 rpm, then it is unfavorable since the mechanical control of the rotation would be difficult. The measurement time may be one within which the potential value may become almost stable, and is preferably shorter. In general, the time may be from 10 to 40 minutes or so.

Figure 1:
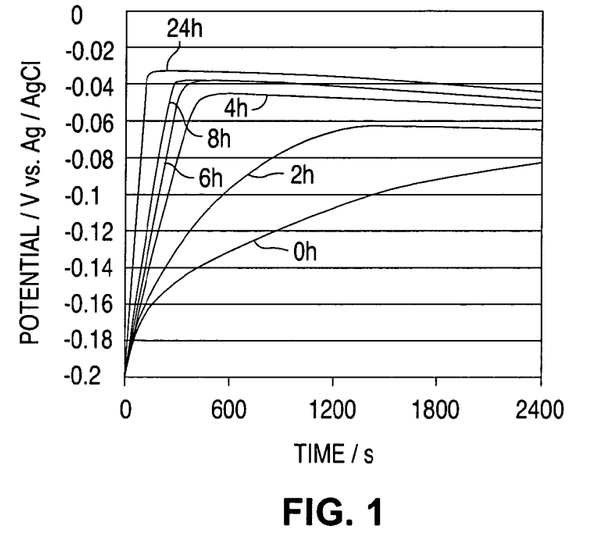
FIG. 1 is a graph showing the result of measurement of the constant-current potential of a plating solution in which the phosphorus-containing copper dipping time is varied.

FIG. 1 shows the result of potential measurement in constant-current electrolysis of a copper electroplating solution in which the phosphorus-containing copper dipping time is varied. The result is almost the same as the result of potential measurement in the first aspect of the invention. As in FIG. 1, in general, the time-dependent potential change curves greatly change in the initial stage, and tend to reach a constant value with time, but with the prolongation of the phosphorus-containing copper dipping time, the curves separate more from the 0-hour curve. In addition, it is understood that, with the prolongation of the phosphorus-containing copper dipping time, the potential change speed in the initial stage of electrolysis is higher, and the convergent value is shifted more to the positive potential. It is known that the prolongation of the phosphorus-containing copper dipping time worsens the fillability of via-holes, and the time-dependent change curves show a correlation with fillability.

Figure 2:
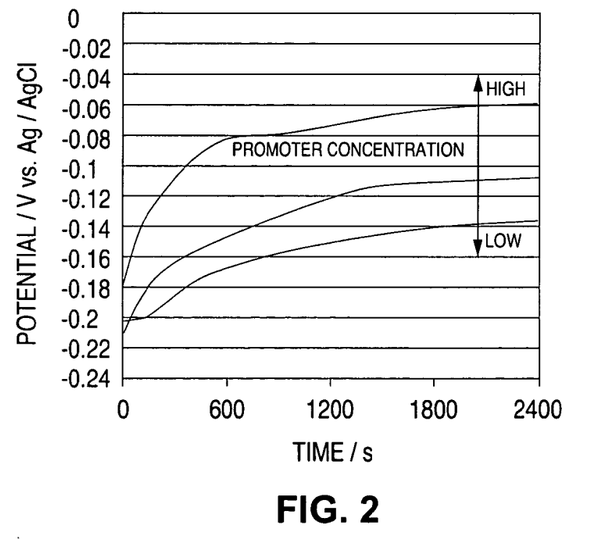
FIG. 2 is a graph showing the result of measurement of the constant-current potential of a plating solution in which the retardant concentration is standard and the promoter concentration is varied.
Figure 3:
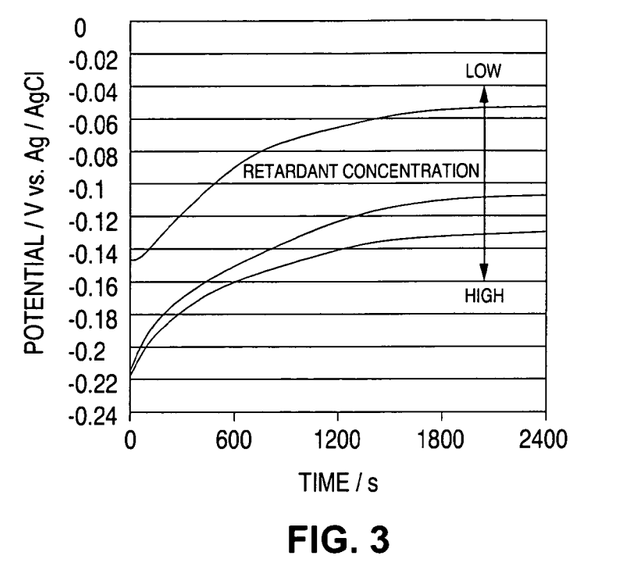
FIG. 3 is a graph showing the result of measurement of the constant-current potential of a plating solution in which the promoter concentration is standard and the retardant concentration is varied.

FIGS. 2 and 3 show the result of measurement of the constant-current potential of a plating solution in which the additive concentration is varied. In these, the solutions tested are all fresh solutions just prepared by adding additives thereto. FIG. 2 shows the result of measurement of the constant-current potential of a plating solution in which the retardant concentration is standard and the promoter concentration is varied. FIG. 3 shows the result of measurement of the constant-current potential of a plating solution in which the promoter concentration is standard and the retardant concentration is varied. When the promoter concentration is increased, then the potential change speed in the initial stage is high and the convergent potential is high. When the retardant concentration is increased, then the potential change speed in the initial stage does not change so much and the convergent potential is low. Accordingly, since the potential change speed in the initial stage of electrolysis changes depending on the additive concentration, it is desirable to use solutions having a controlled additive concentration in CVD for fillability evaluation.

The $1^{st}$ to the $6^{th}$ aspects and the $7^{th}$ to the $12^{th}$ aspects of the invention are for proposing a method and an apparatus for judging fillability in electroplating by determining a time-dependent potential change to obtain time-dependent change curves as in FIG. 1, and using them. One embodiment of the judgment is to use the overall profile of the curves in FIG. 1 to judge the fillability. In FIG. 1, the 0-hour plating solution has the best fillability, and therefore it may be judged that the solutions giving a curve near to the curve profile of the 0-hour plating solution are good.

The characteristics of the curves are further analyzed. Based on the potential change speed in the initial stage of electrolysis and the convergent value as indices, the fillability may be judged. The potential change speed is defined as $(E_1-E_2)/(t_1-t_2)$ where $E_1$ and $E_2$ each are the potential at a certain time $t_1$, and $t_2(t_1<t_2)$, respectively. The convergent value is defined as a potential $E_3$ at a certain time $t_3$ ($t_3>t_1, t_2$) at which the potential change speed is the lowest within the test period. The suitable values of $t_1$, $t_2$ and $t_3$ vary depending on the system to which the method is applied, and therefore they may be suitably settled in accordance with the practicability thereof.

Figure 4:
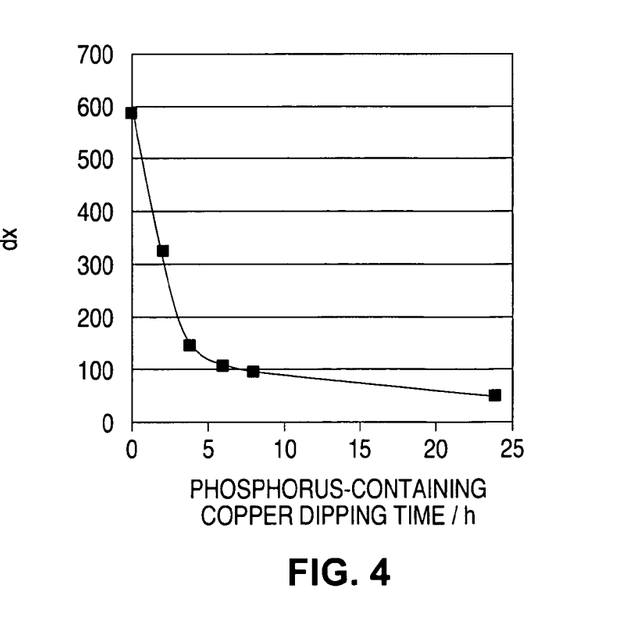
FIG. 4 is a graph showing the change of dx relative to the dipping time in the result of measurement of the constant-current potential in FIG. 1.
Figure 5:
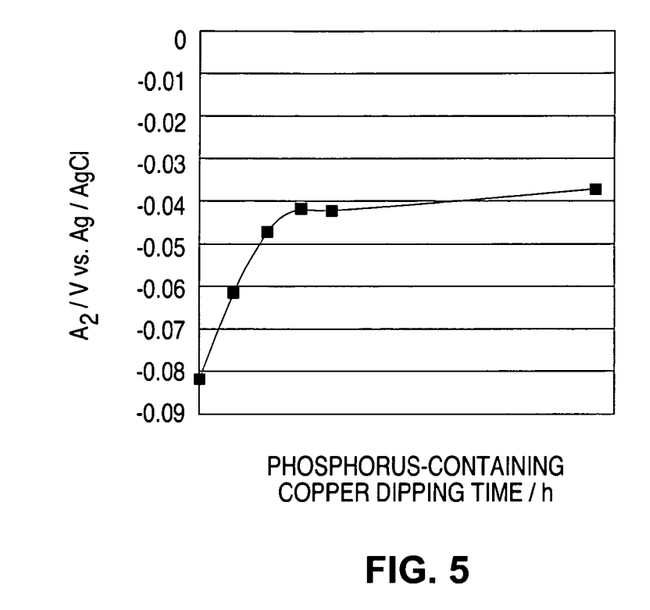
FIG. 5 is a graph showing the change of $A_2$ relative to the dipping time in the result of measurement of the potential in constant-current electrolysis in FIG. 1.

In addition, the time-dependent change curve is approximated to the Boltzmann's function represented by the above-mentioned numerical formula (1), to thereby obtain the potential change speed dx and the potential convergent point A2, and the fillability is thereby quantitatively judged. FIG. 4 shows the relationship between dx obtained from the data in FIG. 1 and the phosphorus-containing copper-dipping time. When the phosphorus-containing copper-dipping time is longer and the potential change speed in the initial stage is higher, then dx is smaller. When dx is smaller, then it may be judged that the fillability is bad. FIG. 5 shows the data $A_2$ obtained similarly. When the phosphorus-containing copper-dipping time is loner and $A_2$ is nearer to a positive level, then it may be judged that the fillability is bad. For fitting the time-dependent change curve to the Boltzmann's function, usable is a commercially-available software for analysis.

Figure 6:
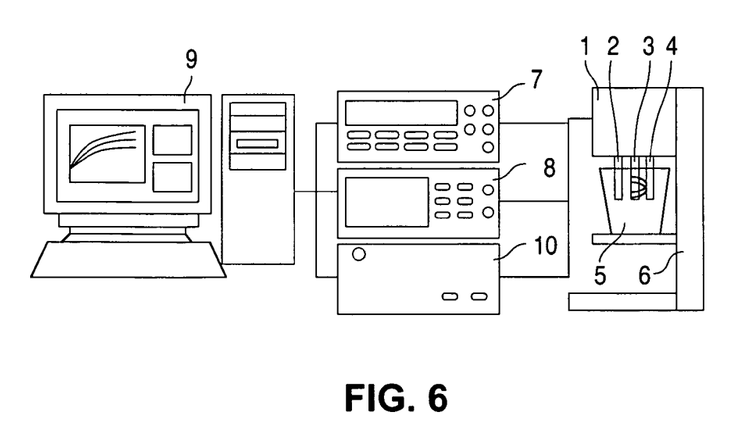
FIG. 6 is an explanatory view showing one example of an apparatus for analyzing a copper electroplating solution.

FIG. 6 is a drawing showing one example of an apparatus for analysis of a copper electroplating solution according to the $5^{th}$ or the $11^{th}$ aspect of the invention. This is the same as one example of the apparatus for analysis of a copper electroplating according to the first aspect of the invention. The number of rotations of the working electrode (rotary electrode) is controlled by the control computer 9 via the controller 10 to be driven only for it. In the rotation-variable stirring unit 1, the rotation should be controllable within a range of 100-7500 rpm. Under computer control, an electric current is applied to the electrochemical cell from the voltage/current generator unit 8, and the potential is measured by the multimeter 7. According to the measurement condition, the constant-current potential measurement is started, and the measured data are displayed in real time and the data collection is started. After the measurement has ended and the data collection has finished, then the time-dependent potential change curve is displayed on the monitor of the control computer, and this may be compared with the previously-recorded curve of a solution having good fillability. In addition, in the control computer 9, the data are computed based on the designated data region, and the potential change speed, the convergent point, and dx and $A_2$ in approximation to the Boltzmann's function are displayed.

Using the method and the apparatus of the $1^{st}$ to the $6^{th}$ aspects and the $7^{th}$ to the $12^{th}$ aspects of the invention, the via fillability with a copper electroplating solution in a semiconductor product can be judged. As a result, when it is judged that the solution condition is not good and satisfactory fillability could not be obtained, then the solution condition must be controlled in order that the time-dependent change curve of the solution could be near to the original condition thereof. For this control, the following methods may be taken. [0057]
(1) Control of additive concentration:

The additive components, promoter and retardant are suitably added. The time-dependent potential change curve may be shifted to the positive direction when a promoter is added but to the negative direction when a retardant is added. [0059]
(2) Oxidation of copper(I) ion:

When a copper metal such as phosphorus-containing copper anode is dipped in a copper electroplating solution, then the reaction of the additive component with the copper metal produces copper(I) ions, and it is believed that the increase in the copper(I) ion concentration may worsen the fillability. Accordingly, the copper(I) ion is oxidized to copper(II) ion so as to lower the copper(I) ion concentration, whereby the fillability may be improved.

For the oxidation, employable are aeration for aerial oxidation; addition of oxide such as hydrogen peroxide or hypochlorite; and electrolytic oxidation with insoluble anode.

(3) Treatment with Activated Charcoal:

In particular, when a plating solution is used for a long period of time, then the decomposed product of the additive therein may accumulate in the solution and it may have some influence on the fillability. Accordingly, by removing the decomposed product through treatment with activated charcoal, the plating solution may be restored to its original condition. The treatment with activated charcoal may be effected in a batch process or may be effected in a mode of continuous liquid circulation through an activated charcoal filter. In any case, the treatment may be so controlled that the fillability with the treated solution could be optimized. In this stage, a method of making the time-dependent potential change curve of the treated solution nearer to a case having good fillability is the optimization method.

The method for analyzing a copper electroplating solution according to the $13^{th}$ to the $18^{th}$ aspects of the invention is described below. Herein investigated is a method capable of differentiating additive-containing copper electroplating solutions from each other as to whether they are good or not good in point of the deteriorated condition thereof. The composition of the plating solution comprises 75 g/liter of copper sulfate, 190 g/liter of sulfuric acid, and 50 mg/liter of chloride ion. As the additive to it, used is a commercially-available additive to copper plating for printed-wiring boards (Nippon Learonal's Coppergleam ST-901).

As a good solution, used is a fresh solution containing a standard amount of an additive and having been just prepared (hereinafter this is referred to as "fresh solution"). As a bad solution, used is a solution containing a standard amount of an additive and having been used for electroplating operation to a degree of 3000 Ahr/liter or so (hereinafter this is referred to as "deteriorated solution"). This is because, the plating solution is worsened in point of the properties of the film formed with it and of the film thickness uniformity, owing to application of electrolytic load thereto.

In the $13^{th}$ to the $18^{th}$ aspects of the invention, used is an electrochemical cell composed of a working electrode (rotary electrode), a reference electrode and a copper electrode (counter electrode). In this, the working electrode (rotary electrode) serves as a cathode and the rotation of the working electrode (rotary electrode) is controlled in the range of 100-7500 rpm; and, line in the above-mentioned section, an electroplating solution is electrolyzed at a constant current so as to make the cathode current density controlled in the range of 0.1-20 $A/dm^2$, and the time-dependent potential change between the cathode and the reference electrode is determined. As the reference electrode, used is Ag/AgCl or $Hg/Hg_2SO_4$, and as the rotary electrode, used is a platinum disc electrode, to which, however, the invention should not be limited.

The optimum cathode current density at which the difference between a fresh solution and a deteriorated solution could be known varies depending on the balance of the additive components in the solutions, and therefore it is desirable that the optimum cathode current density is defined individually for each plating solution. In general, the cathode current density may controlled in the range of 0.1-20 $A/dm^2$, preferably between 0.1-5 $A/dm^2$. If it is lower than 0.1 $A/dm^2$, then a difference will hardly appear in the measurement results between the solution having good fillability and the solution having poor fillability; but if higher than 5 $A/dm^2$, then the potential could hardly become stable.

The rotation of the working electrode (rotary electrode) during measurement is preferably at least 100 rpm at which the effect of rotation may appear. However, if the rotation is more than 7500 rpm, then it is unfavorable since the mechanical control of the rotation would be difficult. The measurement time may be one within which the potential value may become almost stable, and is preferably shorter. In general, the time may be from 10 to 40 minutes or so.

Figure 7:
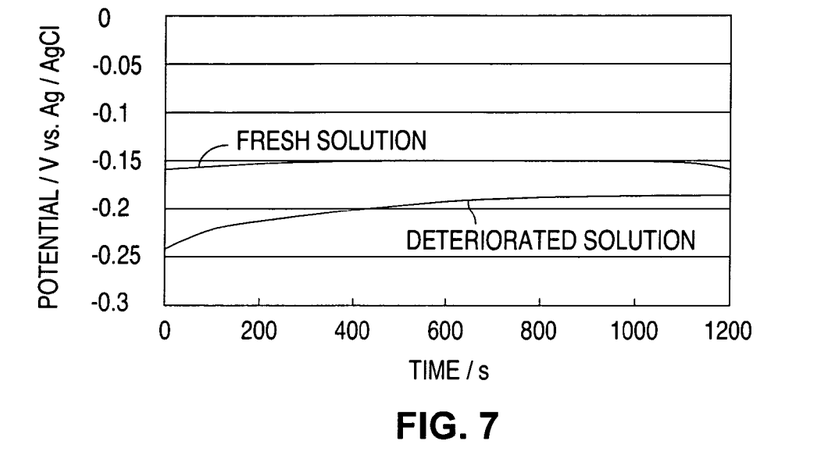
FIG. 7 is a graph showing the result of measurement of the constant-current potential of a fresh solution and a deteriorated solution after electrolysis of about 3000 Ahr/liter.

FIG. 7 shows the result of measurement of the constant-current potential of a fresh solution and a deteriorated solution after electrolysis of about 3000 Ahr/liter. This led to a fact that, with the increase in the electrolysis load after preparation of the plating solution, the potential change speed in the initial stage of electrolysis is higher and the convergent potential is lower. Specifically, it has been found that, from the potential change speed in the initial stage of electrolysis, the influence of the deteriorated condition of the plating solution on the uniformity of electrodeposition thereof (film properties and film thickness uniformity) can be evaluated.

Figure 8:
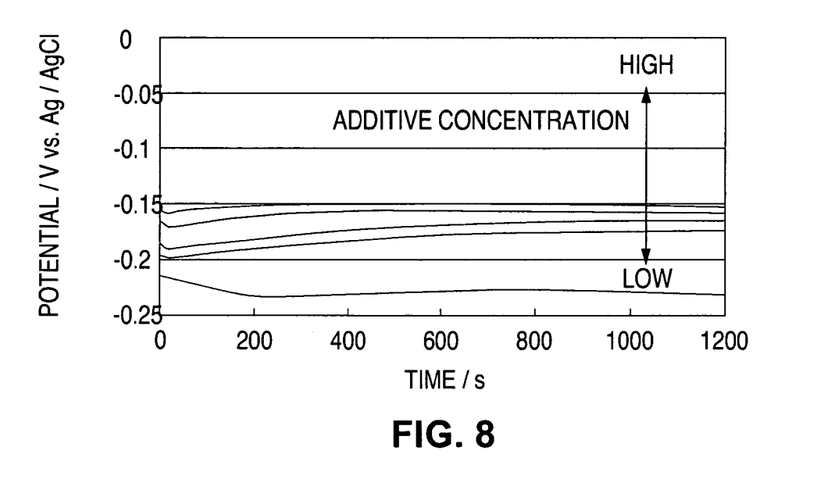
FIG. 8 is a graph showing the result of measurement of the constant-current potential of a plating solution in which the concentration of the additive is varied.

FIG. 8 shows the result of measurement of the constant-current potential of a plating solution in which the additive concentration is varied. The solutions tested are all fresh solutions just prepared by adding additive thereto. When the additive concentration is increased, then the potential change speed in the initial stage is high and the convergent potential is high. Accordingly, since the potential change speed in the initial stage of electrolysis changes depending on the additive concentration, it is desirable to use solutions having a controlled additive concentration in CVD for fillability evaluation.

It is also desirable that the positions of the three electrodes, working electrode (rotary electrode), reference electrode and copper electrode (counter electrode) are all the time fixed during measurement. The potential in constant-current measurement significantly varies depending on the positional relationship of the three electrodes, and therefore, an apparatus in which the three electrodes must be re-set every time when the test solution is exchanged is unfavorable in the invention. Accordingly, for obtaining data of good reproducibility, it is desirable that the three electrodes are fixed in the apparatus used and the test solution can be all the time set in the position in which the three electrodes are all dipped in the solution.

Figure 9:
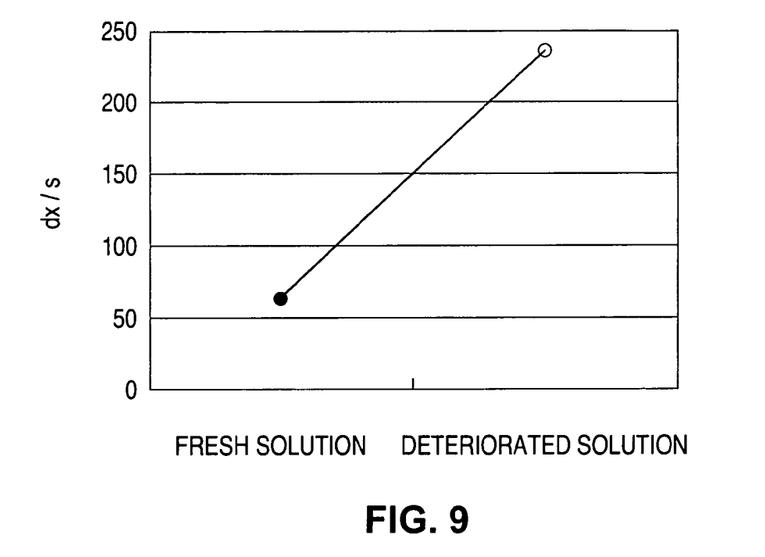
FIG. 9 is a graph showing dx of the result of measurement of the constant-current potential in FIG. 7.

FIG. 9 shows dx of the result of measurement of the constant-current potential in FIG. 7. When the potential change speed in the initial stage is higher, then dx is larger. It is judged that the plating solution having a larger dx is one deteriorated to a higher degree.

The apparatus for analyzing a copper electroplating solution according to the $17^{th}$ aspect of the invention is the same as one example of the apparatus for analyzing a copper electroplating solution according to the $5^{th}$ aspect of the invention, shown in FIG. 6, in which the number of rotations of the working electrode (rotary electrode) is controlled by the control computer via the controller 10 to be driven only for it. In the rotation-variable stirring unit 1, the rotation should be controllable within a range of 100-7500 rpm. According to the measurement condition, the constant-current potential measurement is started, and the measured data are displayed in real time and the data collection is started. After the measurement has ended and the data collection has finished, then the data are computed by the control computer 9 based on the designated data region, and dx is displayed.

The method for analyzing a copper electroplating solution according to the $19^{th}$ to the $21^{st}$ aspects of the invention is described below. Herein investigated is a method capable of differentiating additive-containing copper electroplating solutions from each other as to whether they are good or not good in point of the fillability thereof. The composition of the plating solution comprises 200 g/liter of copper sulfate (5 hydrate), 100 g/liter of sulfuric acid, and 50 mg/liter of chloride ion. As the additives to it, used are an organic sulfur compound as a promoter and a polyether compound as a retardant, and a suitable amount of a quaternary ammonium salt is added to it as a leveler.

When a phosphorus-containing copper anode is dipped in the copper electroplating solution for a long period of time with no current applied thereto, then the fillability with the solution for plating lowers. This is similar to the phenomenon that may occur in a case where an excess promoter is added to the plating solution. It is believed that a substance having a significant promoting effect may be formed in the solution through the reaction between the metal copper in the surface of the phosphorus-containing copper anode and the additive component. However, when the concentration of the additive component of the plating solution is measured through CVS, then both the promoter and the retardant may have nearly the same concentration before and after dipping a phosphorus-containing copper anode in the solution.

Solutions having the same additive component concentration are prepared. Like in the first aspect of the invention, a fresh solution containing a standard amount of an additive and having been just prepared (hereinafter this is referred to as "fresh solution"); and the solution in which a phosphorus-containing copper anode was dipped (hereinafter this is referred to as "phosphorus-containing copper-dipped solution") are used for the measurement test. The phosphorus-containing copper-dipped solution is prepared by setting a controlled area of 100 $cm^2$/liter of a phosphorus-containing copper plate in one liter of the fresh solution, and then statically keeping it as such for 24 and 96 hours.

In the $19^{th}$ to the $21^{st}$ aspects of the invention, used is an electrochemical cell composed of a working electrode (rotary electrode), a reference electrode and a copper electrode (counter electrode). In this, the working electrode (rotary electrode) serves as a cathode and the rotation of the working electrode (rotary electrode) is controlled to in the range of 0-7500 rpm; and an electroplating solution is electrolyzed at a constant current so as to make the cathode current density controlled in the range of 0.1-20 $A/dm^2$, and the time-dependent potential change between the cathode and the reference electrode is determined. As the reference electrode, used is Ag/AgCl or $Hg/Hg_2SO_4$, and as the working electrode (rotary electrode), used is a platinum disc electrode, to which, however, the invention should not be limited.

The optimum cathode current density at which the difference between a fresh solution and a phosphorus-containing copper-dipped solution could be known varies depending on the balance of the additive components in the solutions, and therefore it is desirable that the optimum cathode current density is defined individually for each plating solution. In general, the cathode current density may controlled in the range of 0.1-20 $A/dm^2$, preferably between 0.1-5 $A/dm^2$. If it is lower than 0.1 $A/dm^2$, then a difference will hardly appear in the measurement results between the solution having good fillability and the solution having poor fillability; but if higher than 5 $A/dm^2$, then the potential could hardly become stable.

The rotation of the working electrode (rotary electrode) during measurement may be suitably selected in two stages of 0-7500 rpm. If the rotation is more than 7500 rpm, then it is unfavorable since the mechanical control of the rotation would be difficult. The measurement time may be one within which the potential value may become almost stable, and is preferably shorter. In general, the time may be from 10 to 40 minutes or so.

Figure 10:
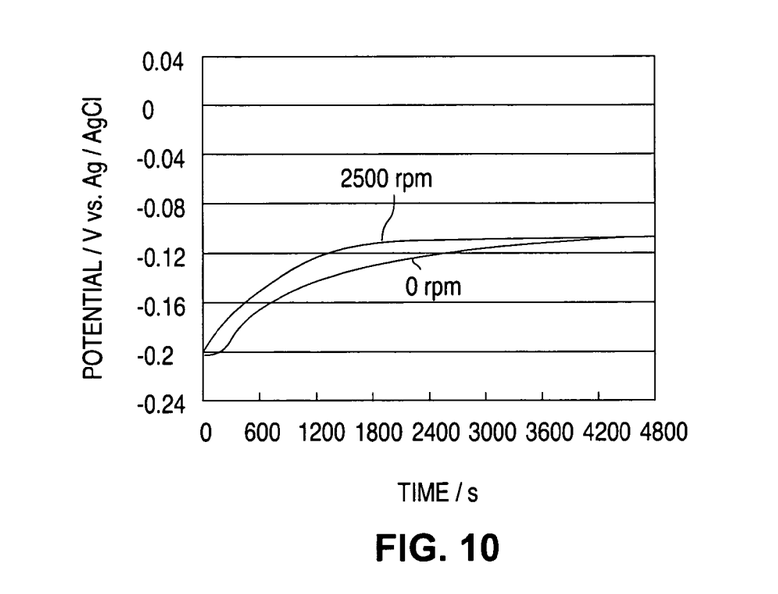
FIG. 10 is a graph showing the result of measurement of the constant-current potential of a plating solution in which phosphorus-containing copper is not dipped as yet.
Figure 11:
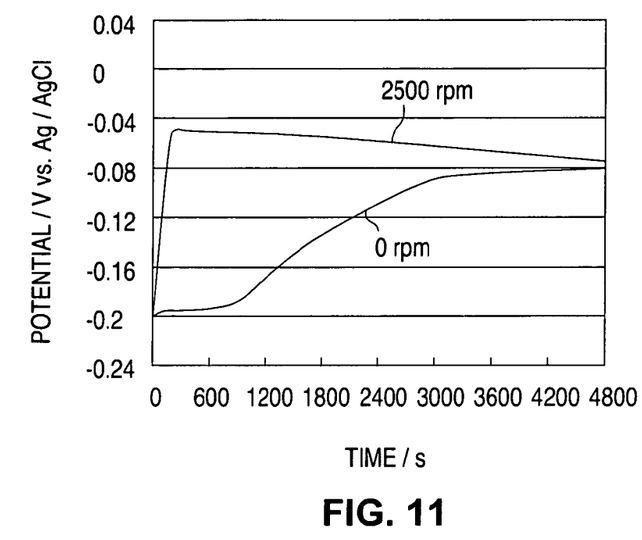
FIG. 11 is a graph showing the result of measurement of the constant-current potential of a plating solution in which phosphorus-containing copper was dipped for 24 hours.
Figure 12:
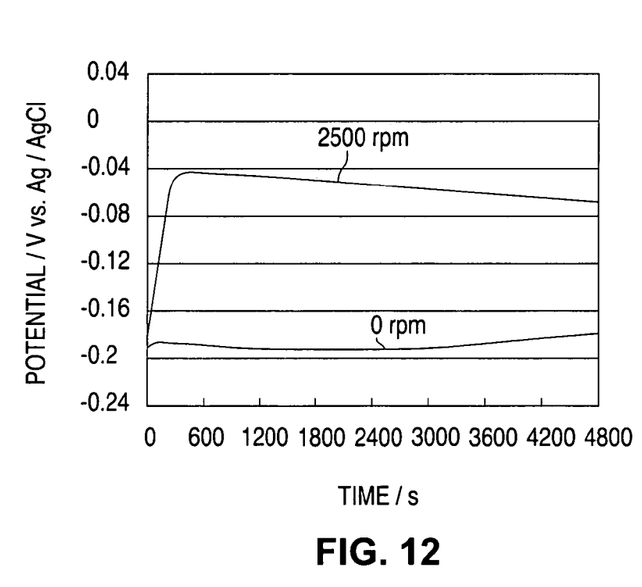
FIG. 12 is a graph showing the result of measurement of the constant-current potential of a plating solution in which phosphorus-containing copper was dipped for 96 hours.

FIG. 10 shows the result of potential measurement in constant-current electrolysis of a fresh solution at a rotation of the working electrode (rotary electrode) of 0 or 2500 rpm. FIG. 11 and FIG. 12 each show the result of the same measurement of the solution in which the phosphorus-containing copper dipping time is 24 or 96 hours. From these, it is understood that the time-dependent potential change curve at two-stage rotation significantly varies depending on the phosphorus-containing copper dipping time.

In ordinary via-filling copper electroplating, the flow rate of the plating solution at around the inlet of a via-hole is large, but inside the via-hole, the flow rate is extremely low. Accordingly, it is believed that, in via-filling plating, the condition having good fillability will be such that the deposition reaction could be retarded under a high flow rate condition but the deposition reaction could be promoted under a low flow rate condition. The condition of deposition reaction retardation or promotion may be detected by potential shifting in the negative or positive direction in the potential measurement.

From FIGS. 10, 11 and 12, it is understood that, when the dipping time is longer, then the potential difference owing to the rotation difference is larger. Since the potential is in the positive direction (for promotion) at a rotation of 2500 rpm and it is in the negative direction (for retardation) at a rotation of 0 rpm, and this is read as the direction in which the fillability lowers. In fact, it is known that, when the phosphorus-containing copper-dipping time is longer, then the via-hole fillability lowers, and the time-dependent change curves well describe the fillability behavior.

FIG. 6 is a drawing showing one example of an apparatus for analysis of a copper electroplating solution according to the $6^{th}$ aspect of the invention. This is the same as one example of the apparatus for analysis of a copper electroplating according to the $5^{th}$ aspect of the invention.

The number of rotations of the working electrode (rotary electrode) is controlled by the control computer 9 via the controller 10 to be driven only for it. In the rotation-variable stirring unit 1, the rotation should be controllable within a range of 0-7500 rpm. According to the measurement condition, the constant-current potential measurement is started, and the measured data are displayed in real time and the data collection is started. After the measurement has ended and the data collection has finished, then the time-dependent potential change curve is displayed on the monitor of the control computer.

Using the method and the apparatus of the $19^{th}$ to the $21^{st}$ aspects of the invention, the via fillability with a copper electroplating solution in a semiconductor product can be judged. As a result, when it is judged that the solution condition is not good and satisfactory fillability could not be obtained, then the solution condition must be restored to a good one. For this control, the above-mentioned methods of (1) control of additive concentration, (2) oxidation of copper (I) ion, and (3) treatment with activated charcoal may be taken, like in the $7^{th}$ to the $12^{th}$ aspects of the invention.

Example 1

The $1^{st}$ to the $6^{th}$ aspects of the invention are described in detail with reference to the following Examples 1 to 3. The apparatus used has the constitution as in FIG. 6. 100 ml of a plating solution of which the additive concentration was controlled through CVS. analysis (plating solution sample 5) was sampled from a via-filling copper plating bath actually in service, and this was put into a beaker and set on a stand 6 for its exclusive use. However, since the plating solution sample changes while left, it was used for the test within 2 days after its sampling.

As the reference electrode 2, used was a two-layer-structured Ag/AgCl reference electrode (the external solution is 10 vol. % $H_2SO_4$; the internal solution is 0. lmol/liter KCl; and Ag/AgCl is in the internal solution, 10 vol. % $H_2SO_4$); as the working electrode 3, used was a platinum rotary electrode (electrode area 4 .pi.$mm^2$); and as the counter electrode 4, used was a copper column (diameter 8 mm).

The electric current was so settled that the current density through the platinum rotary electrode could be 1 $A/dm^2$. The voltage range was .+−.1 V; the current range was 10 mA; the sample distance was 3 s; the rotation of the platinum rotary electrode was 2500 rpm. The test time was 40 minutes. With that, the constant-current potential measurement was started.

After the measurement and the data collection ended, the time-dependent potential change curve was automatically approximated to the above-mentioned Boltzmann's function, and dx was thereby computed. Based on the level of dx, the via fillability with the solution sample was judged.

Example 2

From a via-filling copper plating bath actually in service, the plating solution was sampled at intervals of 2 months, and subjected to constant-current potential measurement under the same condition as in Example 1. The additive concentration of the solution was controlled to be constant through CVS analysis.

Figure 13:
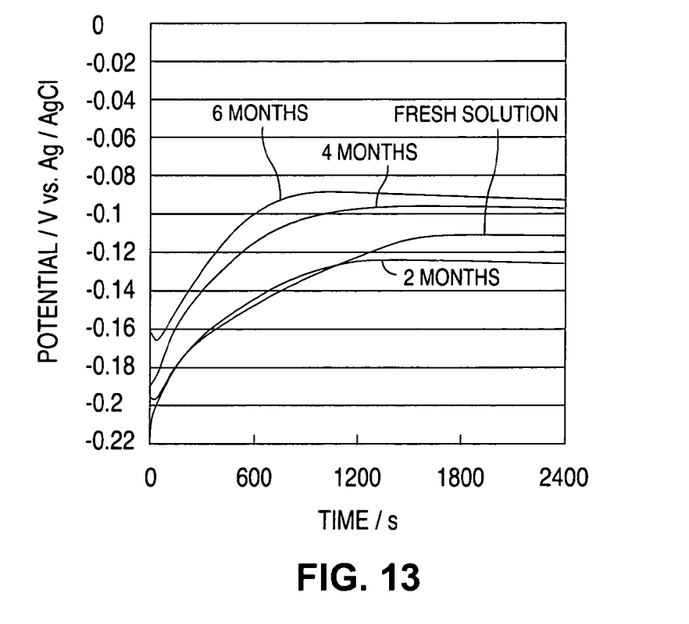
FIG. 13 is a graph showing the result of measurement of the constant-current potential of a fresh plating solution and that of the plating solution measured at intervals of 2 months.
Figure 14:
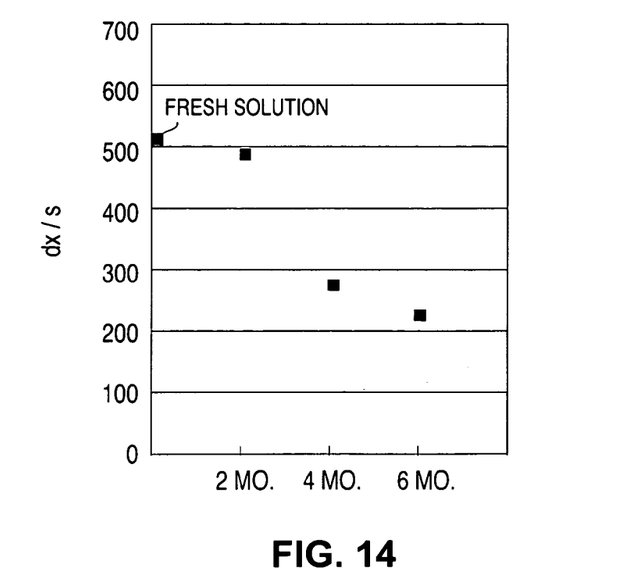
FIG. 14 is a graph showing dx of the result of measurement of the constant-current potential in FIG. 13.

FIG. 13 shows the result of measurement of the constant-current potential of a fresh solution having the same additive concentration as that of the above solution, and that of the plating solution sampled at intervals of 2 months. FIG. 14 shows dx of the result of measurement of the constant-current potential in FIG. 13. From FIGS. 13 and 14, it is understood that, even though the additive concentration was controlled to be constant through CVS analysis, the fillability still lowered.

Example 3

A fresh solution was prepared and divided into two. Nothing was put into one; and a phosphorus-containing copper plate with a controlled area of 100 cm$^2$/liter was put into the other and statically left as it was for 48 hours. Using the two solutions, a via-hole having a diameter of 100 .mu.m and a depth of 75 .mu.m was plated. With the former solution, the via-hole was filled, but not with the latter.

Both solutions were subjected to CVS analysis to determine the promoter concentration and the retardant concentration therein, but the difference between the two was only on a level of error. From this, it may be said that the additive concentration control through CVS analysis is not enough to judge the via fillability.

Example 4

The 7$^{th}$ to the 12$^{th}$ aspects of the invention are described in detail with reference to the following Examples 4 and 5. The apparatus used has the constitution as in FIG. 6.

A copper electroplating solution having a composition of 200 g/liter of copper sulfate (5 hydrate), 100 g/liter of sulfuric acid and 50 mg/liter of chloride ion was prepared, to which were added a suitable amount of an organic sulfur compound, a polyether compound and a quaternary ammonium compound. The fresh solution was divided into two. One was kept as such; and a phosphorus-containing copper plate with a controlled area of 100 cm$^2$/liter was put into the other and statically left as it was for 24 hours. Using the two solutions, a substrate with a via-hole having a diameter of 100 .mu.m and a depth of 75 .mu.m, the surface of which was made electroconductive as having a 1-.mu.m layer made in a mode of electroless copper plating thereon, was plated. With the former solution, the via-hole was filled, but not with the latter. Both solutions were subjected to CVS analysis to determine the promoter concentration and the retardant concentration therein, but there was little difference between the two. From this, it may be said that the additive concentration control through CVS analysis is not enough to judge the via fillability.

The solution was analyzed according to the method of the invention. 100 ml of the plating solution was collected, put into a beaker, and set on a stand 6 for its exclusive use. As the reference electrode 2, used was Ag/AgCl; as the working electrode (rotary electrode) 3, used was a platinum disc electrode (electrode area 4 .pi.mm$^2$); and as the counter electrode 4, used was a copper column (diameter 8 mm).

The electric current was so settled that the current density through the platinum rotary electrode could be 1 A/dm$^2$. The voltage range was .+−.1 V; the current range was 10 mA; the sample distance was 3 s; the rotation of the platinum rotary electrode was 2500 rpm. The test time was 40 minutes. With that, the constant-current potential measurement was started.

After the measurement and the data collection ended, the time-dependent potential change curve was automatically displayed on the monitor panel of a computer. The displayed curves are the same as the time-dependent change curves (0 hr, 24 hrs) in FIG. 1, and they significantly differ from each other in point of their profile. From this, it is confirmed that the difference in the fillability between plating solutions can be detected according to the invention, which, however, could not be detected in CVS analysis.

Further, the time-dependent change curve was approximated to the Boltzmann's function, and dx and A$_2$ were thereby computed. The data are shown in Table 1. It has been confirmed that the solutions of worsened fillability can be judged owing to the reduction in the value dx thereof and to the shifting of the value A$_2$ thereof in the positive direction.
TABLE-US-00001 TABLE 1 0 hr 24 hrs dx 586 46 A$_2$ (V vs. Ag/AgCl) −0.082 −0.036

Example 5

From a via-filling copperplating bath actually in service, the plating solution was sampled at intervals of 2 months, and subjected to constant-current potential measurement under the same condition as in Example 4. The additive concentration of the solution was controlled to be constant through CVS analysis. For comparison, a fresh solution of which the additive concentration was controlled in the same manner was subjected to the same measurement.

Figure 15:
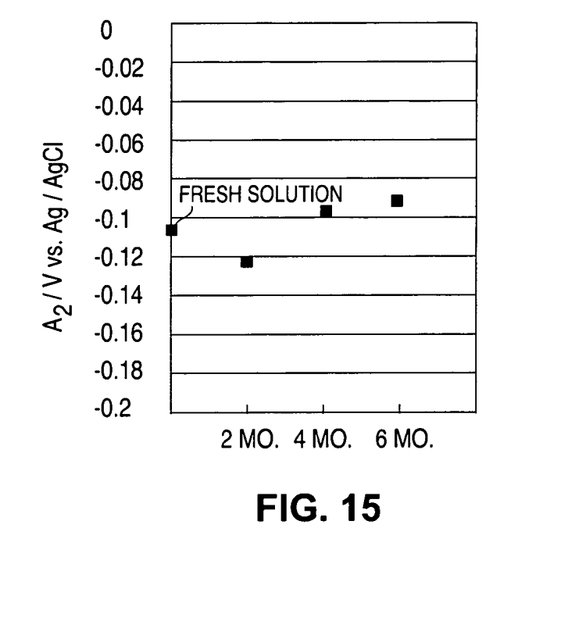
FIG. 15 is a graph showing $A_2$ of the result of measurement of the constant-current potential in FIG. 13.

FIG. 13 shows the result of measurement of the constant-current potential of a fresh solution having the same additive concentration as that of the above solution, and that of the plating solution sampled at intervals of 2 months. The results were the same as those in Example 2. FIGS. 14 and 15 show dx and A$_2$, respectively, of the result of the potential measurement in constant-current electrolysis of FIG. 13. As in FIG. 13, the time-dependent potential change curve profile varies even though the additive concentration was controlled to be constant through CVS analysis. This confirms that the method of the invention gives information which could not be obtained in CVS analysis.

Regarding the via-hole fillability with the solution, the solution sample collected in 6 months gave a hollowed profile at around the mouth of the via-hole and its fillability was insufficient. As in FIGS. 7 and 9, the data dx and A$_2$ vary. By detecting and controlling these data, the fillability of the solution could be evaluated.

Example 6

The 13$^{th}$ to the 18$^{th}$ aspects of the invention are described in detail with reference to the following Examples 6 and 7. The apparatus used has the constitution as in FIG. 6.

100 ml of a plating solution of which the additive concentration was controlled through CVS analysis was sampled from a copper plating bath actually in service for through-hole plating, and this was put into a beaker and set on a stand 6 for its exclusive use. The plating solution sample was used for the test within 2 days after its sampling.

The solution was analyzed according to the method of the invention. 100 ml of the plating solution was sampled, put into a beaker and set on a stand 6 for its exclusive use. As the reference electrode 2, used was Ag/AgCl reference electrode; as the working electrode (rotaryelectrode) 3, used was a platinum disc electrode (electrode area 4 .pi.mm$^2$); and as the counter electrode 4, used was a copper column (diameter 8 mm).

Figure 16:
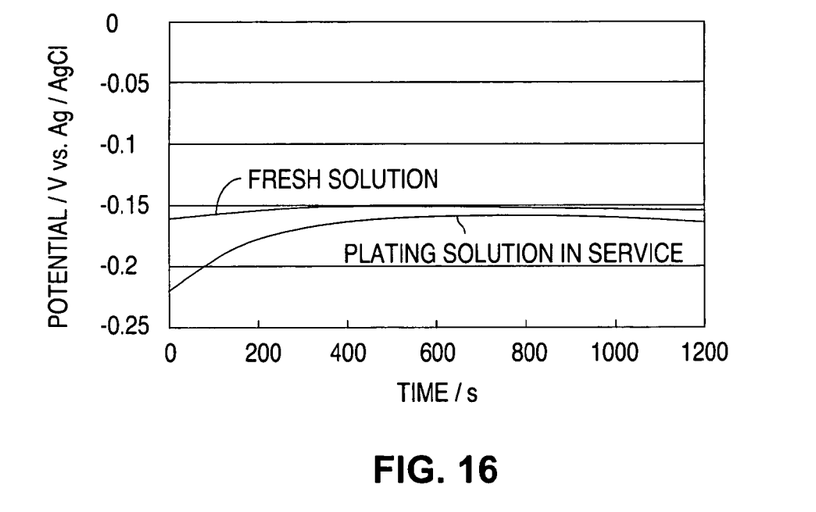
FIG. 16 is a graph showing the result of measurement of the constant-current potential of a plating solution sampled from a copper plating bath in working for through-hole plating.

The electric current was so settled that the current density through the platinum rotary electrode could be 1 A/dm$^2$. The voltage range was .+−.1 V; the current range was 10 mA; the sample distance was 3 s; the rotation of the platinum rotary electrode was 2500 rpm. The test time was 20 minutes. With that, the constant-current potential measurement was started. FIG. 16 shows the result of the measurement of the constant-current potential of the above plating solution.

After the measurement and the data collection ended, the time-dependent potential change curve was automatically approximated to the above-mentioned Boltzmann's function, and dx was thereby computed. Based on the level of dx, the deteriorated condition of the solution sample was judged.

Example 7

A fresh solution was prepared and divided into two. One was used for electrolysis at about 5000 Ahr/liter, and the resulting deteriorated solution was used. The two solutions were subjected to constant-current potential measurement under the same condition as in Example 6. The additive concentration of the two solutions was controlled to be constant through CVS analysis.

Figure 17:
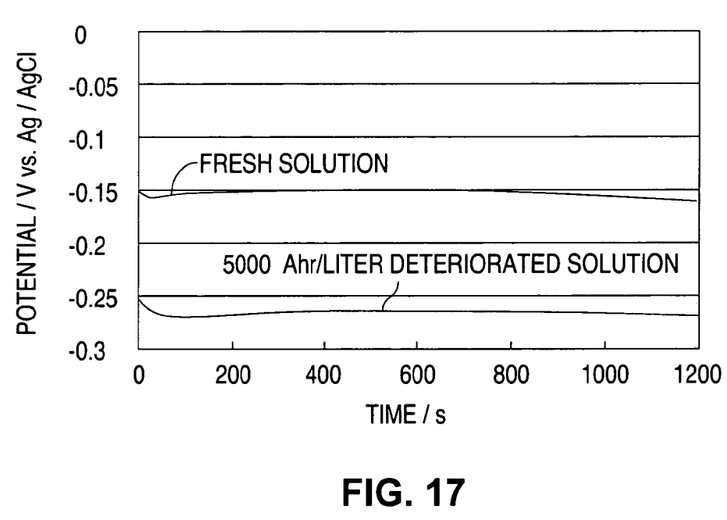
FIG. 17 is a graph showing the result of measurement of the constant-current potential of a fresh solution and a deteriorated solution after electrolysis of about 5000 Ahr/liter.

FIG. 17 shows the result of the constant-current potential measurement of the fresh solution having the same additive concentration as above, and that of the deteriorated solution after electrolysis at about 5000 Ahr/liter. It is understood that, even though the additive concentration is controlled to be constant through CVS analysis, the worsened condition of the plating solution became further worsened.

Using the two solutions, a via-hole having a diameter of 100 .mu.m and a depth of 75 .mu.m was plated. The solutions were investigated for the film properties and the throwing power. The former had a throwing power of about 73%, a tensile strength of 312 N/mm$^2$, a ductility of 19%, and a hardness of 121 Hv; while the latter had a throwing power of about 51%, a tensile strength of 302 N/mm$^2$, a ductility of 15.6%, and a hardness of 120 Hv. In point of the throwing powder and the ductility, the deterioration of the latter was found.

Example 8

The 19$^{th}$ to the 21$^{st}$ aspects of the invention are described in detail with reference to the following Example 8. The apparatus used has the constitution as in FIG. 6.

A copper electroplating solution having a composition of 200 g/liter of cupper sulfate (5 hydrate), 100 g/liter of sulfuric acid and 50 mg/liter of chloride ion was prepared, to which were added a suitable amount of an organic sulfur compound, a polyether compound and a quaternary ammonium compound. The fresh solution was divided into two. One was kept as such; and a phosphorus-containing copper plate with a controlled area of 100 cm$^2$/liter was put into the other and statically left as it was for 96 hours.

Using the two solutions, a substrate with a via-hole having a diameter of 100.mu.m and a depth of 75 .mu.m, the surface of which was made electroconductive as having a 1-.mu.m layer made in a mode of electroless copper plating thereon, was plated. With the former solution, the via-hole was filled, but not with the latter. Both solutions were subjected to CVS analysis to determine the promoter concentration and the retardant concentration therein, but there was little difference between the two. From this, it may be said that the additive concentration control through CVS analysis is not enough to judge the via fillability.

The solution was analyzed according to the method of the invention. 100 ml of the plating solution was collected, put into a beaker, and set on a stand 6 for its exclusive use. As the reference electrode 2, used was Ag/AgCl; as the working electrode (rotary electrode) 3, used was a platinum disc electrode (electrode area 4 .pi.mm$^2$); and as the counter electrode 4, used was a copper column (diameter 8 mm).

The electric current was so settled that the current density through the platinum rotary electrode could be 1 A/dm$^2$. The voltage range was .+-..1 V; the current range was 10 mA; the sample distance was 3 s; the rotation of the platinum rotary electrode was first 0 rpm, and then it was 2500 rpm after the solution sample exchange. The test time was 40 minutes.

FIG. 10 shows the result of the test with the fresh solution; and FIG. 12 shows the result of the test with the solution in which the phosphorus-containing copper was dipped for 96 hours. From this, it is confirmed that the difference in the fillability between plating solutions can be detected according to the invention, which, however, could not be detected in CVS analysis.

As described in detail herein above with reference to Examples, the 1$^{st}$ to the 6$^{th}$ aspects of the invention have solved the problem with plating solutions in that the fillability with aged plating solutions worsens even though the additive concentration therein is controlled through CVS analysis. According to the analysis of the invention, it has become possible to judge the plating solutions having the same additive concentration in CVS analysis as to whether their fillability is good or not good. When the fillability of a plating solution is judged not good as a result of the analysis of the invention, then the additive may be removed from the solution or an additional additive may be added to the solution, and the invention has made it possible to more accurately control a plating solution to a higher level.

The 7$^{th}$ to the 12$^{th}$ aspects of the invention have solved the problem with copper electroplating solutions to be used for filling a via-hole with a copper metal in a mode of copper electroplating, in that the via fillability worsens owing to the time-dependent change of the plating solution. According to the analysis of the invention, it has become possible to judge the plating solutions having the same additive concentration in CVS analysis as to whether their fillability is good or not good. When the fillability of a plating solution is judged not good as a result of the analysis of the invention, then the additive concentration of the solution may be controlled or the solution may be oxidized or treated with activated charcoal, and the invention has made it possible to more accurately control a plating solution to a higher level.

The 13$^{th}$ to the 18$^{th}$ aspects of the invention have solved the problem with plating solutions in that the film properties and the uniformity worsen even though the additive concentration in the solutions is controlled through CVS analysis. According to the analysis of the invention, it has become possible to judge the plating solutions having the same additive concentration in CVS analysis as to whether their fillability is good or not good. When the uniformity of electrodeposition (film properties and film thickness uniformity) of a plating solution is judged not good as a result of the analysis of the invention, then the additive may be removed from the solution or an additional additive may be added to the solution, and the invention has made it possible to more accurately control a plating solution to a higher level.

The 19$^{th}$ to the 21$^{st}$ aspects of the invention have solved the problem with copper electroplating solutions to be used for filling a via-hole with a copper metal in a mode of copper electroplating, in that the via fillability worsens owing to the time-dependent change of the plating solution. According to the analysis of the invention, it has become possible, to judge the plating solutions having the same additive concentration in CVS analysis as to whether their fillability is good or not good. When the fillability of a plating solution is judged not good as a result of the analysis of the invention, then the additive concentration of the solution may be controlled or the solution may be oxidized or treated with activated charcoal in order that the time-dependent change curve profile of the solution maybe nearer to the original profile thereof, and the invention has made it possible to more accurately control a plating solution to a higher level.

Industrial Applicability

Application examples of the invention include copper electroplating solutions used for filling a copper metal in a via-hole or a trench installed in printed circuit boards, semiconductor package substrates or semiconductor products such as semiconductor substrates, and the invention provides a method for analyzing the solutions that require higher level control and provides an apparatus for the analysis.

What is claimed:

1. A method for analyzing a copper electroplating solution containing an additive, which comprises determining the time-dependent potential change at a cathode current density of $0.1\text{-}20 A/dm^2$ to thereby judge the fillability with the copper electroplating solution, wherein the time-dependent potential change determination is effected while a rotation of a working electrode is controlled in the range of 100-7500 rpm, and wherein the fillability is judged by obtaining the potential change speed in the initial stage of electrolysis and the potential convergent point from the time-dependent potential change curve for a predetermined period of time after the start of the electrolysis.

* * * * *